United States Patent [19]
Ogawa et al.

[11] Patent Number: 4,694,076
[45] Date of Patent: Sep. 15, 1987

[54] SIALIC ACID DERIVATIVES

[75] Inventors: Tomoya Ogawa, Musashino; Mamoru Sugimoto, Niiza; Yoshiyasu Shitori, Musashino; Masayoshi Ito, Kunitachi, all of Japan

[73] Assignees: Kanto Ishi Pharmaceutical Co., Ltd., Tokyo; Rikagaku Kenkyusho, Wako, both of Japan

[21] Appl. No.: 680,498

[22] Filed: Dec. 11, 1984

[51] Int. Cl.[4] .................................. C07H 5/06
[52] U.S. Cl. .................. 536/17.2; 536/18.6; 536/4.1
[58] Field of Search .................. 536/17.2, 18.6

[56] References Cited

U.S. PATENT DOCUMENTS 4,238,473 12/1980 Lemieux et al. ............ 536/17.2
4,374,832 2/1983 Joseph et al. ............... 536/4.1

FOREIGN PATENT DOCUMENTS 59-164798 9/1984 Japan.

OTHER PUBLICATIONS

*The Merck Index*, 9th Ed. 1976, No. 8225, p. 1098.

*Primary Examiner*—Johnnie R. Brown
*Assistant Examiner*—Elli Peselev
*Attorney, Agent, or Firm*—Oblon, Fisher, Spivak, McClelland, & Maier

[57] ABSTRACT

Sialic acid derivatives of the formula:

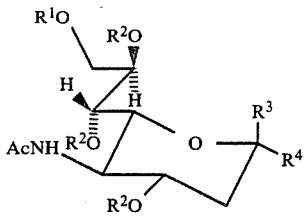

wherein $R^1$ is hydrogen, trityl, or acyl, $R^2$ is hydrogen or acyl, $R^3$ and $R^4$ are individually glycerolglycoside, dialkylglycerol, alkoxycarbonyl or carboxyl.

These compounds may be employed as a useful intermediate for the synthesis of biologically active substances and may be employed as an inhibitor of hydrolytic enzyme, a reagent for affinity chromatography for purifying enzyme, or a synthetic antigen.

14 Claims, No Drawings

SIALIC ACID DERIVATIVES

BACKGROUND OF THE INVENTION

This invention relates to new sialic acid derivatives and in particular, to new sialoylglycolipid which contains biologically active sialic acid at the non-reducing terminal and a method for producing the same.

DESCRIPTION OF THE PRIOR ART

Sialic acid exists in free or combined form with sialoylglycoconjugate such as glycoprotein, glycolipid, oligosaccharide, polysaccharide, etc. in the surface of animal or bacterial cell and much attention is now forcused thereon from a medical and pharmacological point of view as a compound involved in immunity, cancer, inflammation, virosis, cytodieresis, hormone receptor, etc.

With increase in use of chemotherapeutics such as adrenocortical hormone or immunosuppressant for the treatment of various diseases such as carcinosis, hypoimmunity and many kinds of side effects are observed and therefore, it is becoming more difficult to treat a subject suffering from such diseases as cancer.

SUMMARY OF THE INVENTION

The inventors of this invention have paid attention to the importance of sialic acid, which is one of inherent constituents of animal living body, as a marker on the cell surface and have conducted reactions of sialic acid halide as a glycosyl donor with various glycosyl acceptors. As a result, they have succeeded in synthesis of new sialic acid derivatives which are expected to cause no side effect and to possess many physiological activities such as adaptation of immunoresponse and have accomplished this invention.

This invention provides sialic acid derivatives of the formula described below and the mthod for producing the same.

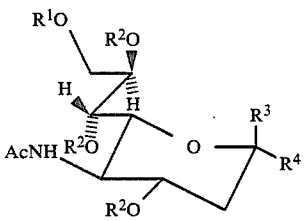

wherein $R^1$ is hydrogen, trityl, or acyl, $R^2$ is hydrogen or acyl, $R^3$ and $R^4$ are individually glycerolglycoside, dialkylglycerol, alkoxycarbonyl or carboxyl.

The term "alkoxycarbonyl" herein is used to represent methoxycarbonyl or ethoxycarbonyl.

DETAILED DESCRIPTION OF THE INVENTION

The sialic acid derivatives of the above formula according to the present invention can be prepared by reacting the glycosyl donor of the formula (2'), which can be derived from sialic acid by a conventional method, with various glycosyl acceptors prepared by a conventional method.

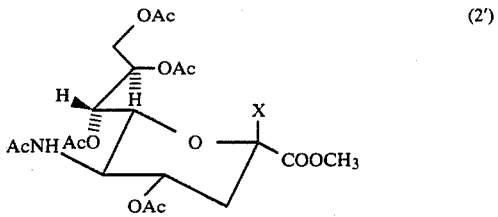

wherein X represents halogen, preferably Cl or Br.

The glycosyl donor (2), the starting compound of the present invention, can be derived from sialic acid methyl ester peracetate (1) by Kuhn et al method (Chem. Ber., 99, 611–617 (1966)).

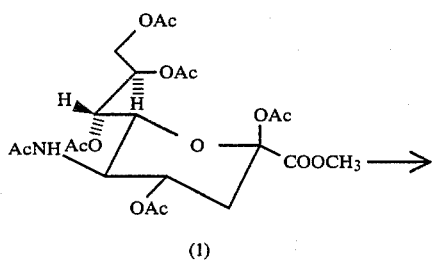

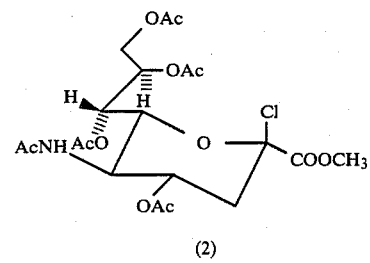

One of the glycosyl acceptor (6) can be derived from the compound (3) of the formula (3) by Ogawa et al method [Agr. Biol. Chem., 46(1), 255–262 (1982)]. More specifically, the compound (3) is reacted with triphenylmethyl chloride (trityl chloride) to form 6-O-trityl derivative (4) which is then acetylated to form 2,3,4-tri-O-acetyl-derivative (5), the trityl group of which is then removed to give the compound (6).

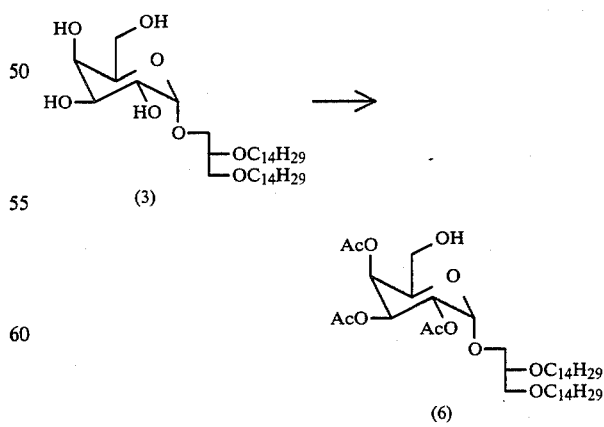

The glycosyl donor (2) can be reacted with the glycosyl acceptor such as the compound (6) to obtain various glycolipids. For example, the glycosyl acceptor (6) is reacted with the glycosyl donor (2) in such solvent as dichloromethane, 1,2-dichloroethane, etc. in the presence of glycosidation catalyst such as Hg(CN)$_2$, HgBr$_2$, molecular sieves, Ag$_2$CO$_3$, AgClO$_4$, AgOSO$_2$CF$_3$, (CH$_3$)$_3$COSO$_2$CF$_3$, etc. at −20° C. to 150° C., preferably −5° C. to 20° C., for 1 to 120 hours, preferably 1 to 5 hours to give the compounds (7) and (8) (hereinafter, the name of a compound is represented by the number of the compound as shown in Examples hereinbelow) which can be deacetylatzed by a conventional manner, for example, using NaOHC$_3$/CH$_3$OH to give the compounds (7′) and (8′).

The compound (2) is reacted with 1,2-di-O-tetradecyl-Sn-glycerol in the presence of the glycosidation catalyst such as Hg(CN)$_2$ and HgBr$_2$ to give the compound (9) (β-anomer) and the compound (10) (α-anomer). The compound (10) is deacetylated by alkali such as NaOCH$_3$ to give the compound (11), which is reacted with trityl chloride to give the compound (12), which is acetylated by acetic anhydride to the compound (13), which is then detritylated to give the compound (14). The compound (14) is reacted with the compound (2) in the presence of the glycosidation catalyst such as Hg(CN)$_2$ and HgBr$_2$ to give the compounds (15-a) and (15-b), which are separated and then deacetylated to give the compounds (15′) and (15″), respectively.

Similarly, the compound (9) is deacetylated by alkali such as NaOCH$_3$ to give the compound (16). All the compounds (7), (7′), (8), (8′), (9), (10), (11), (12), (13), (14), (15-a), (15-b), (15′), (15″) and (16) thus obtained are new and have never been disclosed in any references.

These compounds of the present invention may be employed as a useful intermediate for the synthesis of various biologically active substances and may be used as an inhibitor of hydrolytic enzyme, a reagent for affinity chromatography for purifying enzyme, or a synthetic antigen. It is also expected that they may clinically be used as an immunity associated agent which is involved in the adaptation of immunoresponse.

The present invention will now be explained in detail with reference to the following Examples, to which the present invention is not restricted.

EXAMPLE 1

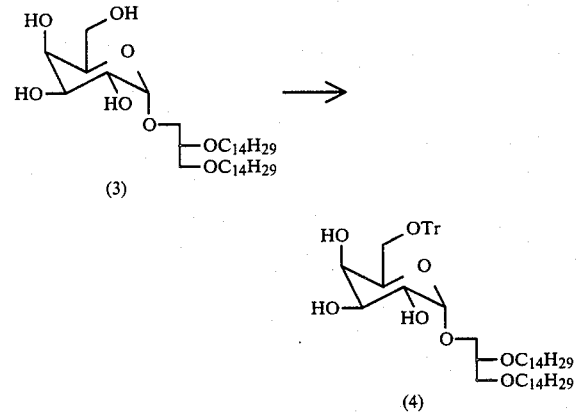

3-O-(α-D-Galactopyranosyl)-1,2-di-O-tetradecyl-Sn-glycerol (3) (647 mg) was dissolved in pyridine (5 ml). Trityl chloride (558 mg) was added to the solution. The mixture was stirred at 60° C. for 7 hours and concentrated in vacuo. The residue was subjected to column chromatography (SiO$_2$, C-300, 50 g) and eluted with 5% methanol-containing chloroform to obtain 3-O-(6-O-trityl-α-D-galactopyranosyl)-1,2-di-O-tetradecyl-Sn-glycerol (4) (758 mg, 85.2%).

Analysis: Calcd. for C$_{37}$H$_{74}$O$_8$: C; 75.63, H; 9.97. Found: C; 75.63, H; 9.90.

$[\alpha]_D^{21°} +35.0°$ (C=1.06, CHCl$_3$).

EXAMPLE 2

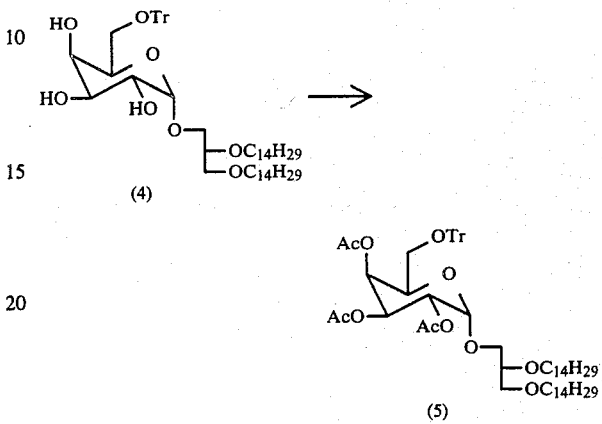

3-O-(6-O-trityl-α-D-galactopyranosyl)-1,2-di-O-tetra-decyl-Sn-glycerol (4) (672 mg) was dissolved in acetic anhydride (3 ml) and pyridine (3 ml). The solution was stirred at room temperature for 24 hours and concentrated in vacuo. The residue was subjected to column chromatography (Wakogel C-300, 70 g) and eluted with 0.5% methanol-containing chloroform to obtain 3-O-(2,3,4-tri-O-acetyl-6-O-trityl-α-D-galactopyranosyl)-1,2-di-O-tetradecyl-Sn-glycerol (5) (740 mg, 96.4%).

Analysis: Calcd. for C$_{62}$H$_{94}$O$_{11}$: C; 73.33, H; 9.33. Found: C; 73.34, H; 9.14.

$[\alpha]_D^{21°} +33.0°$ (C=1.29, CHCl$_3$).

EXAMPLE 3

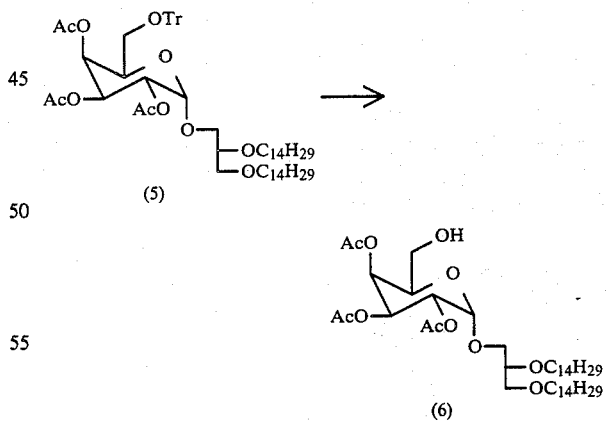

3-O-(2,3,4-tri-O-acetyl-6-O-trityl-α-D-galactopyranosyl)-1,2-di-O-tetradecyl-Sn-glycerol (5) (599 mg) was mixed with 90% acetic acid (30 ml). The mixture was stirred at 50° C. for 2 hours and concentrated in vacuo. The residue was subjected to column chromatography (Wakogel C-300, 120 g) and eluted with 2.5% methanol-containing chloroform to obtain 3-O-(2,3,4-tri-O-acetyl-α-D-galactopyranosyl)-1,2-di-O-tetradecyl-Sn-glycerol (6) (255 mg, 60.8%).

Analysis: Calcd. for $C_{43}H_{80}O_{11}$: C; 66.81, H; 10.43. Found: C; 66.89, H; 10.42.
$[\alpha]_D^{21°} +69.6°$ (C=1.0, CHCl$_3$).

EXAMPLE 4

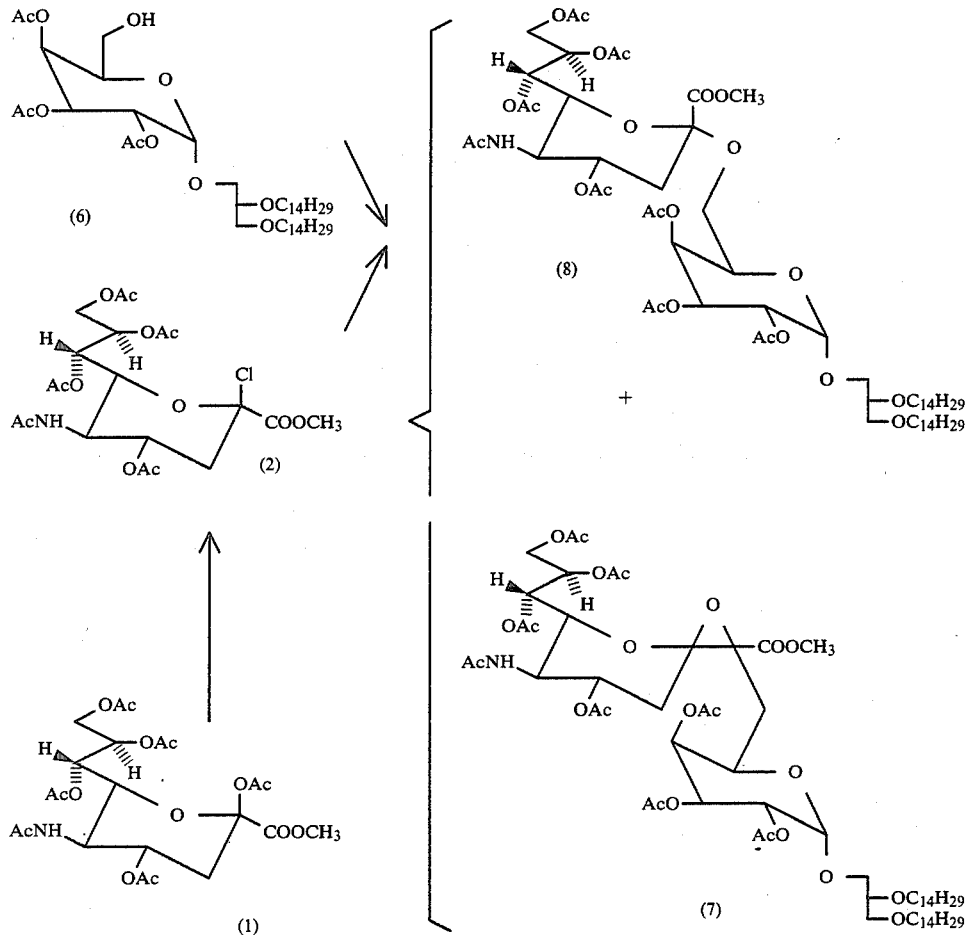

The compound (2) derived from the methyl ester peracetate (1) (54 mg) and 3-O-(2,3,4-tri-O-acetyl-α-d-galactopyranosyl)-1,2-di-O-tetradecyl-Sn-glycerol (6) (77 mg) were dissolved in 1,2-dichloroethane (2 ml). Hg(CN)$_2$ (50 mg), HgBr$_2$ (72 mg) and freshly dried molecular sieves 4 A (100 mg) were added to the solution which was then stirred for 2 days under argon atmosphere. The reaction mixture was filtered to remove insolubles. The filtrate was concentrated in vacuo. The residue was subjected to column chromatography (Wakogel C-300, 10 g) to obtain a mixture of 1,2-di-O-tetradecyl-3-O-[2,3,4-tri-O-acetyl-6-O-methyl(5-acetamido-4,7,8,9-tetra-O-acetyl-3,5-dideoxy-β-D-glycero-D-galacto-2-nonuropyranosyl)onate]Sn-glycerol (B 7) and 1,2-di-O-tetradecyl-3-O-[2,3,4-tri-O-acetyl-6-O-methyl(5-acetamido-4,7,8,9-tetra-O-acetyl-3.5-dideoxy-α-D-glycero-D-galacto-2-nonuropyranosyl)onate]-Sn-glycerol (8) (42 mg) which mixture was eluted with 1.5% methanol-containing chloroform to obtain β,α-anomer (7) (11 mg) and α,α-anomer (8) (4 mg).

The compound (7):
$[\alpha]_D^{21°} +37.5°$ (C=0.57, CHCl$_3$).
NMR: $\delta_{400\ MHz}^{ppm}$ (CDCl$_3$) 2.45, /H, q J=11.7, 4.9 Hz (3H, eq); 1.82, t J=11.7 Hz (3H, ax).

The compound (8):
$[\alpha]_D^{21°} +31.5°$ (C=0.20, CHCl$_3$).
NMR: $\delta_{400}^{ppm}$ (CDCl$_3$) 2.53, /H, q J=12.9, 4.6 Hz (3H, eq); 1.91, t J=12.5 Hz (3H, ax).

EXAMPLE 5

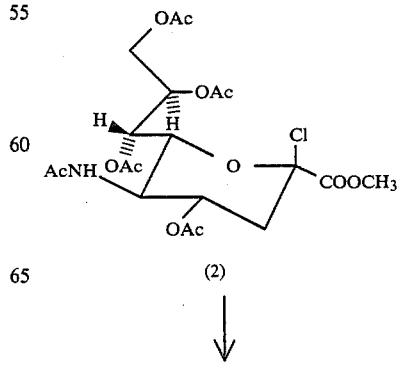

-continued

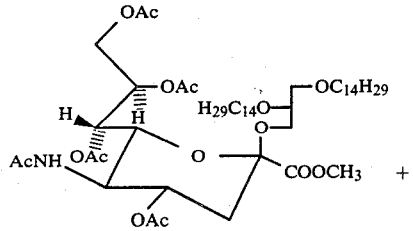

(9)

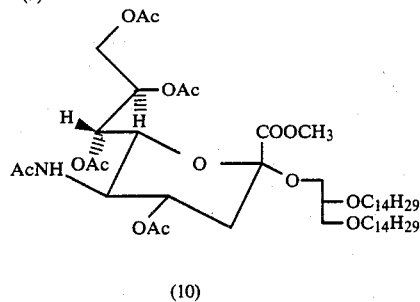

(10)

The compound (2) freshly prepared from the compound (1) (533 mg) was dissolved in 1,2-dichloroethane (15 ml). 1,2-di-O-tetradecyl-Sn-glycerol (485 mg), Hg(CN)$_2$ (505 mg), HgBr$_2$ (721 mg) and freshly dried molecular sieves 4 A (1.0 g) were added to the solution which was then stirred at room temperature for 48 hours under argon atmosphere. The reaction mixture was filtered to remove insolubles. The filtrate was concentrated in vacuo. The residue was subjected to column chromatography (Wakogel C-300, 150 g) and eluted with toluene-ethyl acetate to obtain β-anomer (9) (225 mg, 23.5%) and α-anomer (10) (353 mg, 36.8%).

3-O-[methyl(5-acetamido-4,7,8,9-tetra-O-acetyl-3,5-dideoxy-β-D-glycero-D-galacto-2-nonuropyranosyl)onate]-1,2-di-O-tetradecyl-Sn-glycerol (9).

$[\alpha]_D^{23°} -13.0°$ (C=1.0, CHCl$_3$).

Analysis: Calcd. for C$_{51}$H$_{91}$NO$_{15}$: C; 63.92, H; 9.57, N; 1.46. Found: C; 63.64, H; 9.54 N; 1.48.

NMR: $\delta_{400}^{ppm}$ (CDCl$_3$) 2.45, /H, q J=4.8, 12.5 (3H, eq); 1.90, /H, t J=12.2 (3H, ax).

3-O-[methyl(5-acetamido-4,7,8,9-tetra-O-acetyl-3,5-dideoxy-β-D-glycero-D-galacto-2-nonuropyranosyl)onate]-1,2-di-O-tetradecyl-Sn-glycerol (10).

$[\alpha]_D^{23°} -9.3°$ (C=1.04, CHCl$_3$).

Analysis: Calcd. for C$_{51}$H$_{91}$NO$_{15}$: C; 63.92, H; 9.57, N; 1.46. Found: C; 64.01, H; 9.42 N; 1.45.

NMR: $\delta_{400}^{ppm}$ (CDCl$_3$) 2.60, /H, q J=4.8, 13.1 (3H, eq); 1.97, /H, t J=12.8 (3H, ax).

EXAMPLE 6

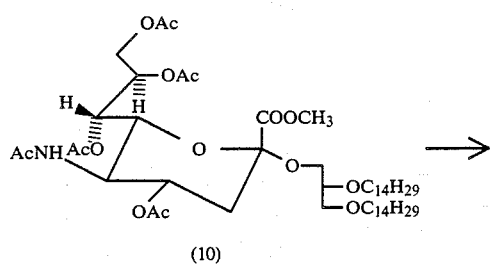

(10)

-continued

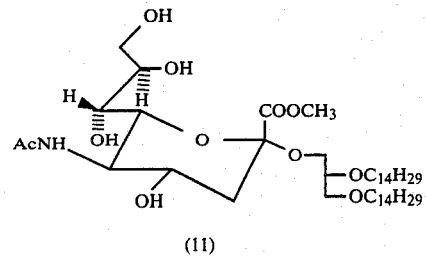

(11)

The compound (10) (342 mg) was dissolved in methanol (5 ml), to which N-NaOCH$_3$ (0.35 ml) was added. The mixture was stirred to room temperature for one hour. AMBERLYST A-15 (registered trademark) was added to neutralize the reaction mixture which was then filtered and concentrated in vacuo to obtain 3-O-[methyl(5-acetamido-3,5-dideoxy-α-D-glycero-D-galacto-2-nonuropyranosyl)onate]-1,2-tetradecyl-Sn-glycerol (11) (189 mg, 67%) as powder precipitated.
m.p. 108°–109° C.

Analysis: Calcd. for C$_{43}$H$_{83}$NO$_{11}$: C; 65.36, H; 10.59, N; 1.77. Found C; 65.56, H; 10.49, N; 1.71.

$[\alpha]_D^{22°} -5.20°$ (C=1.0, CHCl$_3$).

EXAMPLE 7

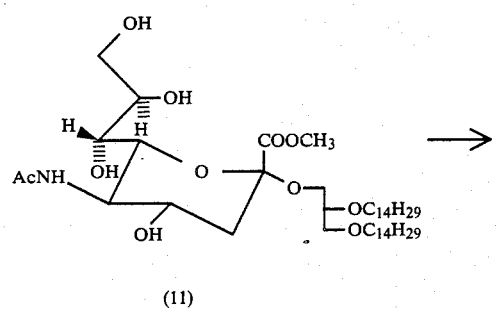

(11)

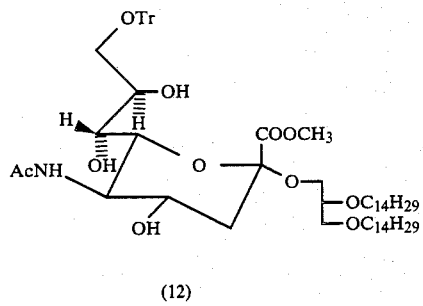

(12)

The compound (11) (2.26 g) was dissolved in pyridine (28 ml) and trityl chloride (1.59 g) was added thereto. The mixture was stirred at 50° C. for 6 hours. The reaction mixture was dried on MgSO$_4$ and concentrated in vacuo. The residue was subjected to column chromatography (Wakogel C-300, 300 g) and eluted with ethyl acetate to obtain 3-O-[methyl(5-acetamido-3,5-dideoxy-6-O-trityl-α-D-glycero-D-galacto-2-nonuropyranosyl)onate]-1,2-tetradecyl-Sn-glycerol (12) (2.81 g, 96.3%).

Analysis: Calcd. C; 72.98, H; 8.40, N; 1.37. Found: C; 71.39, H; 9.22, N; 1.34.

$[\alpha]_D^{22°} -5.20°$ (C=1.0, CHCl$_3$).

EXAMPLE 8

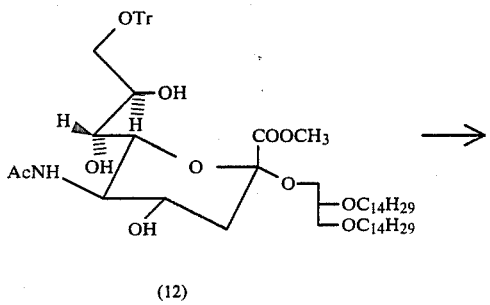

(12)

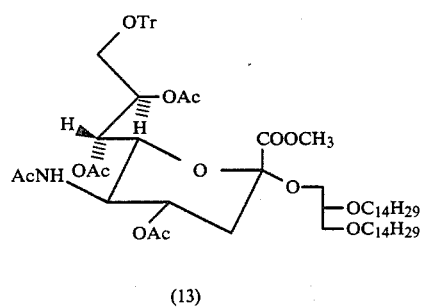

(13)

The compound (12) (1.35 g) was dissolved in pyridine (5 ml) and acetic anhydride (5 ml). The mixture was stirred at room temperature for 24 hours and concentrated in vacuo.

The residue was subjected to column chromatography (Wakogel C-300, 80 g) and eluted with toluene-ethyl acetate (5:2) to obtain 3-O-[methyl(5-acetamido-4,7,8-tri-O-acetyl-6-O-trityl-3,5-dideoxy-α-D-glycero-D-galacto-2-nonuropyranosyl)onate]-1,2-tetradecyl-Sn-glycerol (13) (1.32 g, 86.1%).

Analysis: Calcd. C; 70.49, H; 8.96, N; 1.21. Found: C; 70.52, H; 8.98, N; 1.17.

$[\alpha]_D^{21°} +2.92°$ (C=1.20, CHCl₃).

EXAMPLE 9

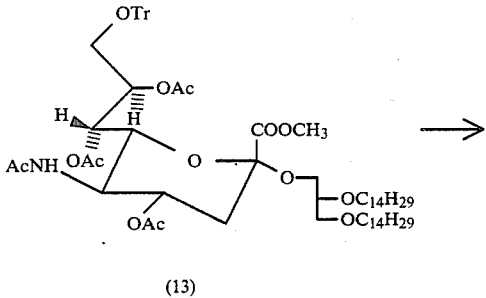

(13)

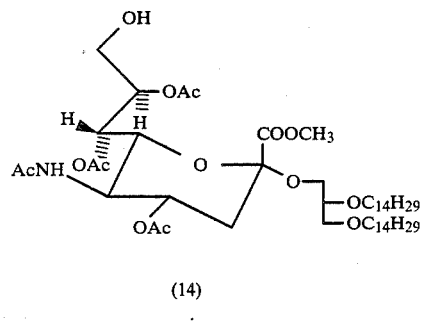

(14)

The compound (13) (1,146 mg) was dissolved in 90% acetic acid. The mixture was stirred at 50° to 60° C. for 2 hours and then concentrated in vacuo. The residue was dissolved in ethyl acetate. The solution was washed with saturated NaHCO₃ solution, then water, dried on MgSO₄ and concentrated in vacuo. The residue was subjected to column chromatography (Wakogel C-300, 80 g) and eluted with toluene-ethyl acetate (1:4) to obtain 3-O-[methyl(5-acetamido-4,7,8-tri-O-acetyl-3,5-dideoxy-α-D-glycero-D-galacto-2-nonuropyranosyl)onate]-1,2-tetradecyl-Sn-glycerol (14) (554 mg, 61.1%).

Analysis: Calcd. C; 64.23, H; 9.79, N; 1.53. Found C; 64.39, H; 9.78, N; 1.53.

$[\alpha]_D^{22°} -17.2°$ (C=0.50, CHCl₃).

EXAMPLE 10

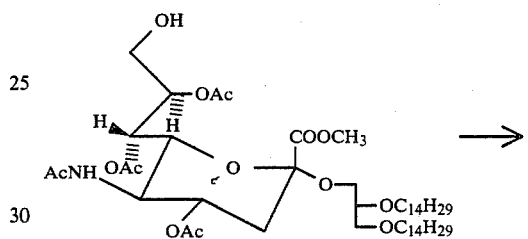

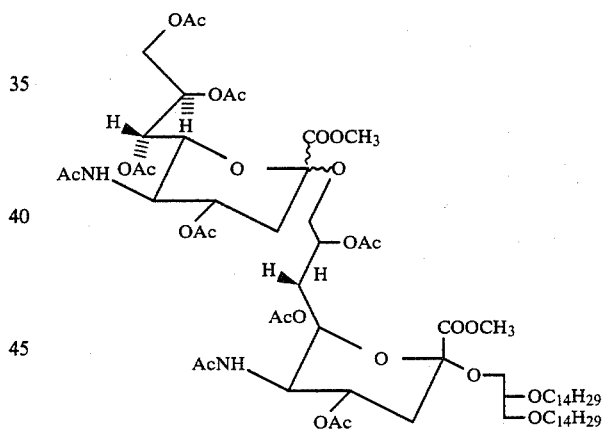

The compound (2) freshly prepared from the compound (1) (128 mg) was dissolved in 1,2-dichloroethane (5 ml). Hg(CN)₂ (121 mg), HgBr₂ (173 mg), the compound (14) (220 mg) and freshly dried molecular sieves 4 A (1.0 g) were added thereto. The reaction mixture was stirred at room temperature for 2 days under argon atmosphere, filtered to remove insolubles and concentrated in vacuo. The residue was subjected to column chromatography (Wakogel C-300, 500 g) and eluted with 3% methanol-containing ethyl acetate to obtain the compounds (15-a) (18 mg) and (15-b) (16 mg).

NMR: $\delta_{90 MHz}^{ppm}$ (CDCl₃):

(15-a) 3.80, 3H, s, —OCH₃; 1.88-2.18, 27H, s, —COCH₃×9; 1.25, 24H, s, —CH₂—×12.

(15-b) 3.80, 3H, s, —OCH₃; 1.88-2.17, 27H, s, —COCH₃×9; 1.25, 24H, s, —CH₂—×12.

EXAMPLE 11

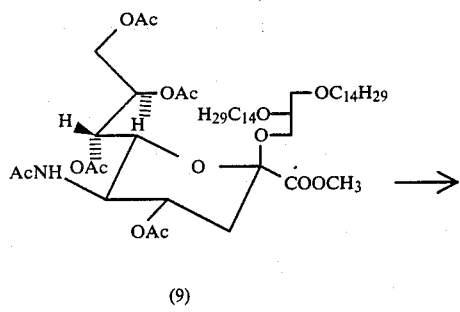

(9)

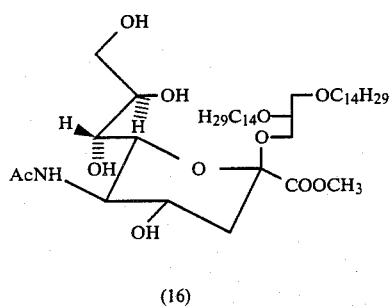

(16)

The compound (9) (225 mg) was dissolved in methanol (5 ml), to which 1N-CH$_3$ONa in methanol (0.3 ml) was added. The reaction mixture was stirred at room temperature for 30 minutes. The product precipitated was filtered and washed with methanol to give the compound (16) (161 mg, 86.8%).

Analysis: Calcd. D; 65.36, H; 10.59, N; 1.77. Found C; 64.56, H; 10.49, N; 1.71.

Example 12

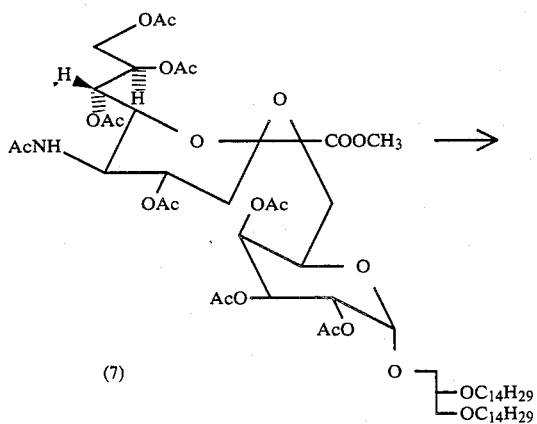

(7)

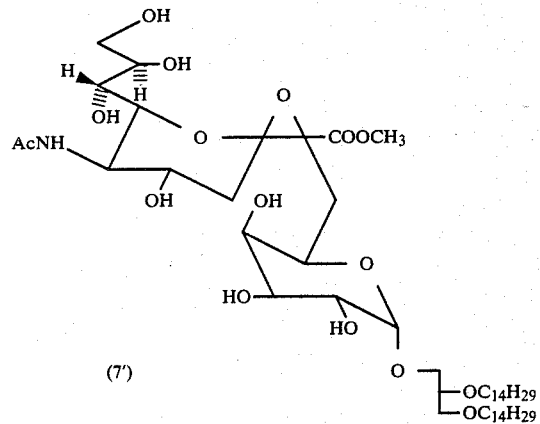

(8)

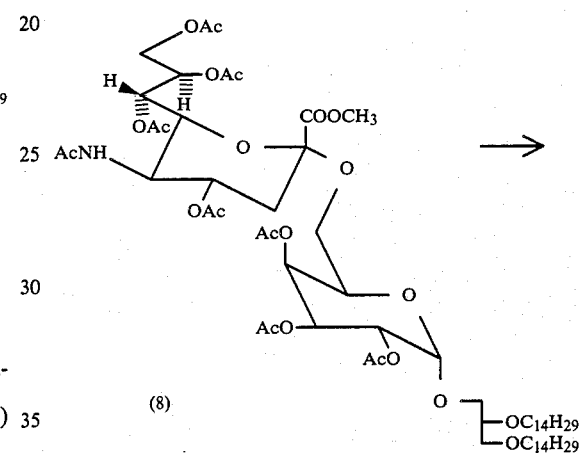

(7')

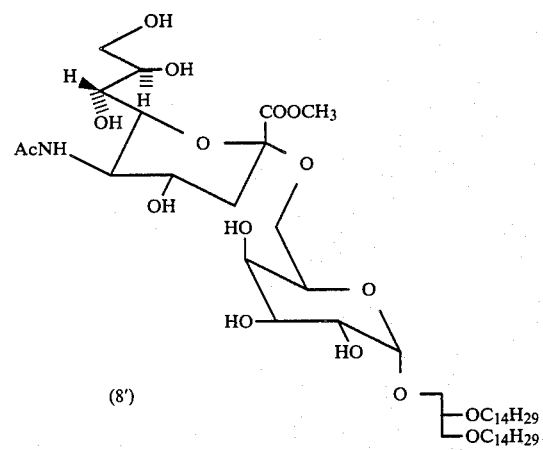

(8')

The compounds (7) (11 mg) and (8) (4 mg) were dissolved in methanol (1.0 ml), respectively. 1N-NaOCH$_3$ in methanol (0.1 ml) was added to each of the solutions which were then stirred at room temperature for 30 minutes. The products precipitated were filtered and washed with methanol to give the compound (7') (5 mg, 60%) and the compound (8') (2 mg, 65%) as powder, respectively.

The compound (7'):

Analysis: Calcd. C; 61.80, H; 9.84, N; 1.47. Found: N; 61.40, H; 9.63, N; 1.37.

NMR: $\delta_{90~MHz}^{ppm}$ (CD$_3$OD) 2.03, 3H, s, —NHCO$\underline{CH}_3$; 3.82, 3H, s, —O$\underline{CH}_3$.

The compound (8'):
Analysis: Calcd. C; 61.80, H; 9.84, N; 1.47. Found C; 61.51, H; 9.95, N; 1.36.
NMR: $\delta_{90\ MHz}^{ppm}$ (CD$_3$OD) 2.03, 3H, s, —NH-COC$\underline{H}_3$; 3.83, 3H, s, —OC$\underline{H}_3$.

EXAMPLE 13

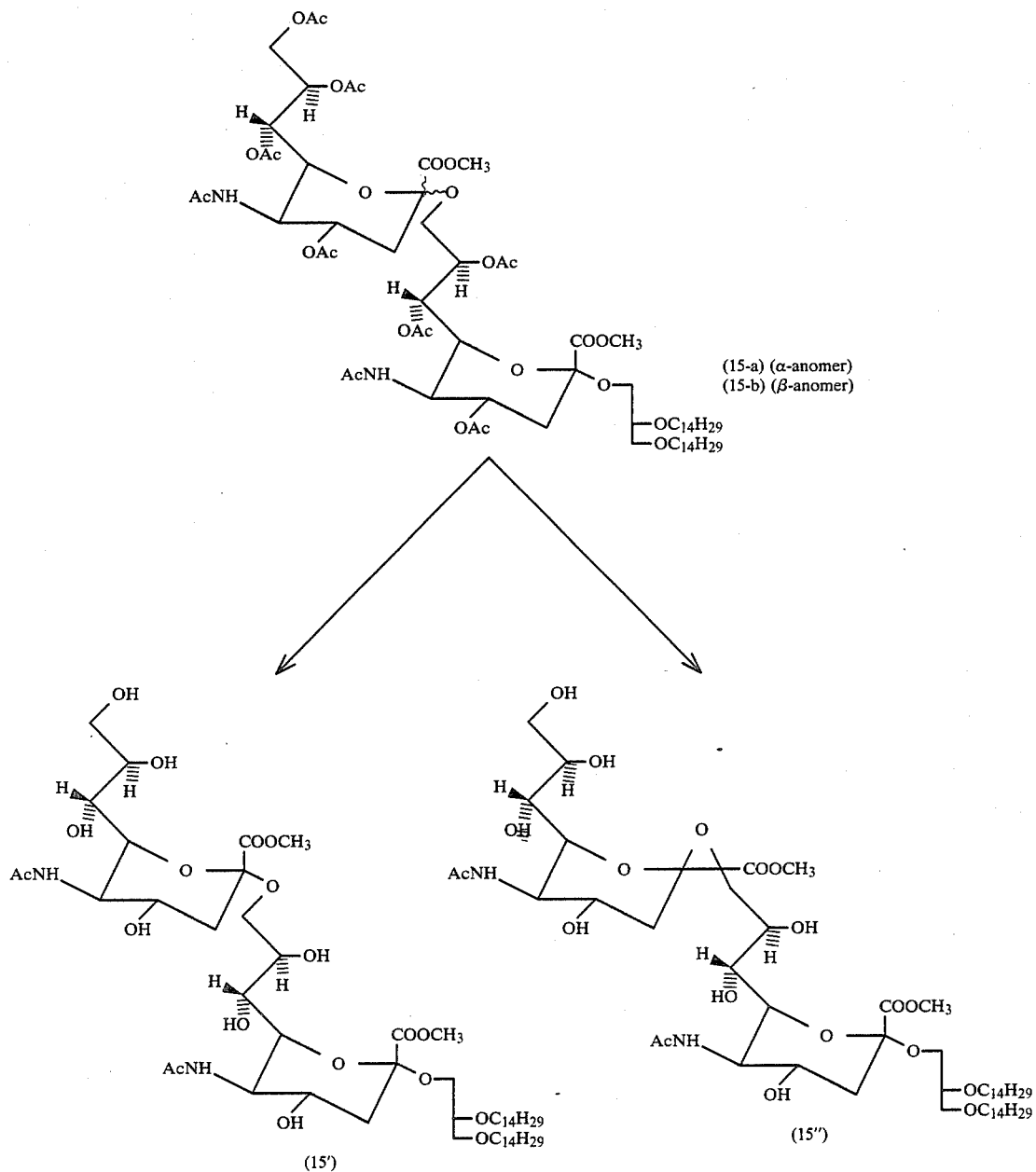

The compounds (15-a) (18 mg) and (15-b) (16 mb) were dissolved in methanol (2 ml). 1N-NaOCH$_3$ in methanol (0.2 ml) was added to each of the solutions which were then stirred at room temperature for 30 minutes. The produces precipitated were filtered and washed with methanol to give the compound (15') (7 mg, 50%) and the compound (15'') (5 mg, 40%) as powder, respectively.

The compound (15'):
NMR: $\delta_{90\ MHz}^{ppm}$ (CD$_3$OD) 2.02, 6H, s, —NH-COC$\underline{H}_3$×2; 3.83, 6H, s, —OC$\underline{H}_3$×2.

Analysis: Calcd. C; 60.30, H; 9.39, N; 2.56. Found C; 59.80, H; 9.10 N; 2.16.

The compound (15''):
NMR: $\delta_{90\ MHz}^{ppm}$ (CD$_3$OD) 2.03, 6H, s, —NH-COC$\underline{H}_3$×2; 3.85, 6H, s, —OC$\underline{H}_3$×2.
Analysis: Calcd. C; 60.30, H; 9.39, N; 2.56. Found C; 59.70, H; 9.30 N; 2.22.

What we claim is:
1. A sialic acid derivative of the formula:

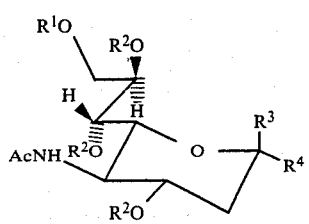

wherein $R^1$ is hydrogen, trityl, or acetyl, $R^2$ is hydrogen or acetyl, one of $R^3$ and $R^4$ is carboxyl, methoxycarbonyl or ethoxycarbonyl, and the other of $R^3$ and $R^4$ is

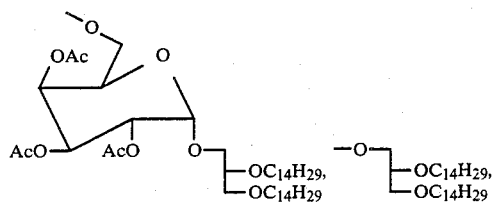

2. The sialic acid derivative of claim 1 of the formula:

[structure with OAc, AcNH, COOCH₃, OC₁₄H₂₉ groups]

wherein Ac is acetyl.

3. The sialic acid derivative of claim 1 of the formula:

[structure with OAc, AcNH, COOCH₃, OC₁₄H₂₉ groups]

wherein Ac is acetyl.

4. The sialic acid derivative of claim 1 of the formula:

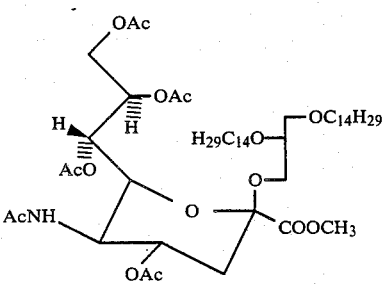

wherein Ac is acetyl.

5. The sialic acid derivative of claim 1 of the formula:

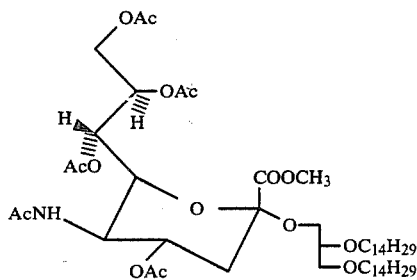

wherein Ac is acetyl.

6. The sialic acid derivative of claim 1 of the formula:

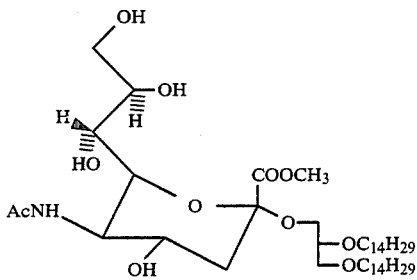

wherein Ac is acetyl.

7. The sialic acid derivative of claim 1 of the formula:

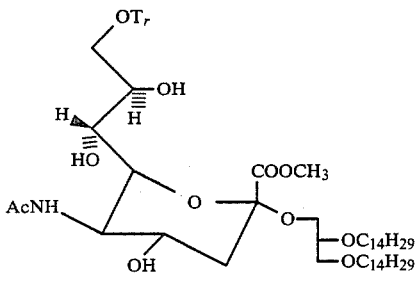

wherein Ac is acetyl, and Tr is trityl.

8. The sialic acid derivative of claim 1 of the formula:

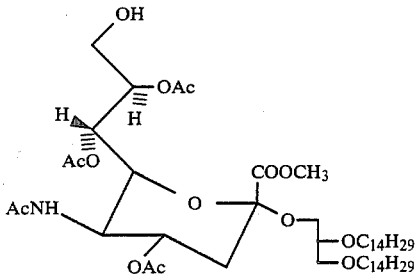

wherein Ac is acetyl, and Tr is trityl.

9. The sialic acid derivative of claim 1 of the formula:

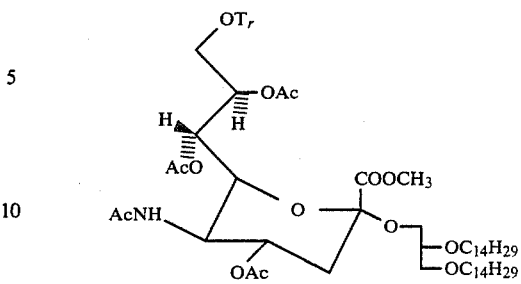

wherein Ac is acetyl.

10. The sialic acid derivative of claim 1 of the formula:

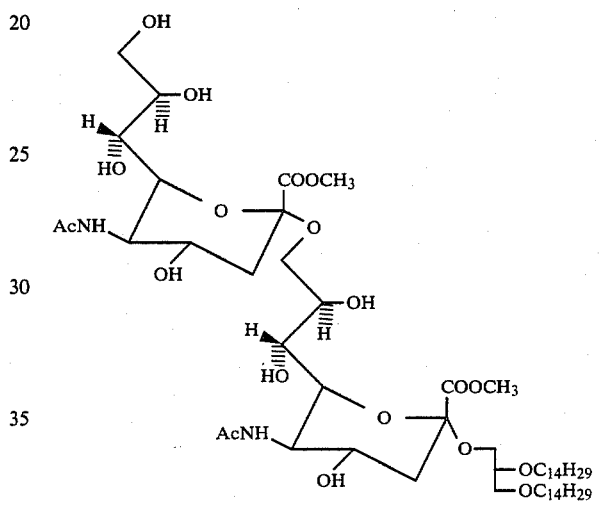

wherein Ac is acetyl.

11. The sialic acid derivative of claim 1 of the formula:

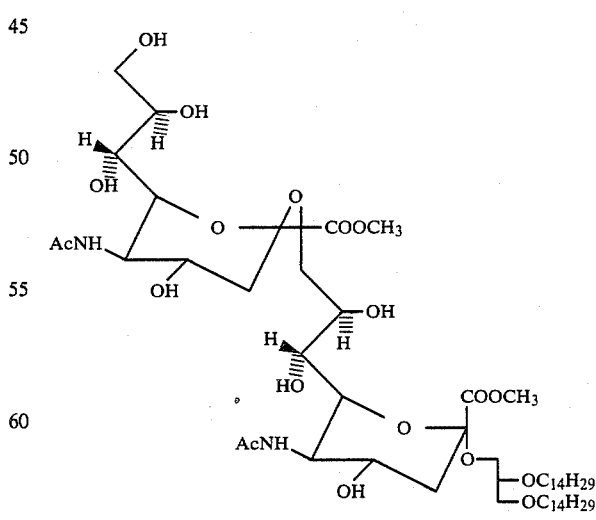

wherein Ac is acetyl.

12. The sialic acid derivative of claim 1 of the formula:

13. The sialic acid derivative of claim 1 of the formula:
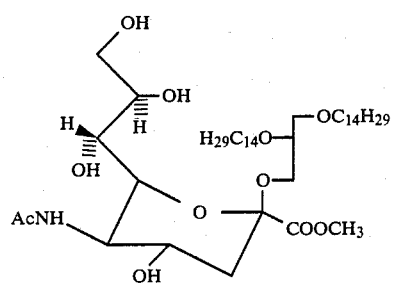
wherein Ac is acetyl.
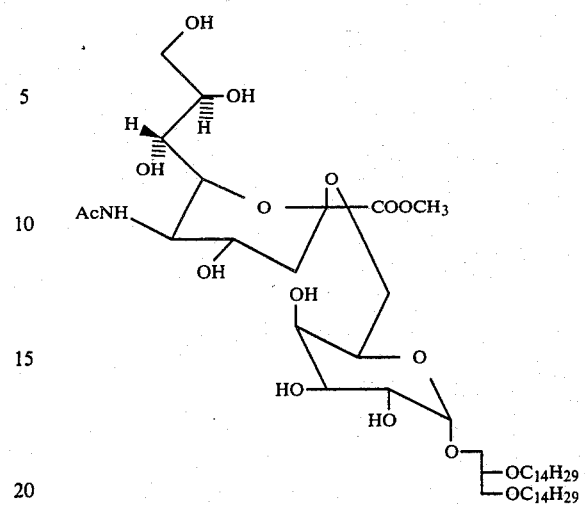
wherein Ac is acetyl.
14. The sialic acid derivative of claim 1 of the formula:
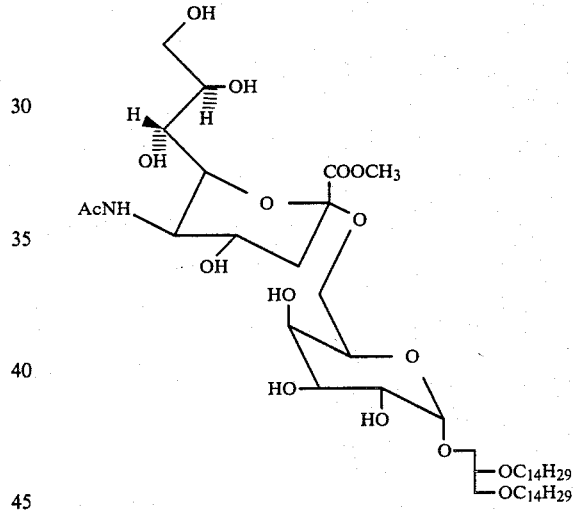
wherein Ac is acetyl.
* * * * *